US006344587B1

(12) United States Patent
Jautelat et al.

(10) Patent No.: US 6,344,587 B1
(45) Date of Patent: Feb. 5, 2002

(54) METHOD FOR PRODUCING TRIAZOLINTHION DERIVATIVES

(75) Inventors: Manfred Jautelat, Burscheid; Achim Hupperts, Düsseldorf; Reinhard Lantzsch, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/795,062

(22) Filed: Feb. 26, 2001

Related U.S. Application Data

(62) Division of application No. 09/509,927, filed as application No. PCT/EP98/06113 on Sep. 25, 1998.

(30) Foreign Application Priority Data

Oct. 8, 1997 (DE) .......................... 197 44 400

(51) Int. Cl.$^7$ ............................................. C07C 337/06
(52) U.S. Cl. ........................................................ 564/18
(58) Field of Search ............................................ 564/18

(56) References Cited

U.S. PATENT DOCUMENTS

| | | | |
|---|---|---|---|
| 4,913,727 A | 4/1990 | Stroech et al. | 71/92 |
| 4,980,488 A | 12/1990 | Stroech et al. | 549/563 |
| 4,988,819 A | 1/1991 | Stroech et al. | 548/267.8 |
| 4,990,677 A | 2/1991 | Stroech et al. | 568/29 |
| 5,034,052 A | 7/1991 | Stroech et al. | 71/92 |
| 5,789,430 A | 8/1998 | Jautelat et al. | 514/272.4 |
| 5,856,495 A | 1/1999 | Weckbecker et al. | 546/272.4 |
| 5,859,039 A | 1/1999 | Jautelat et al. | 514/384 |

FOREIGN PATENT DOCUMENTS

| | | |
|---|---|---|
| DE | 4030039 | 3/1992 |
| DE | 4339412 | 5/1995 |
| DE | 19601189 | 7/1997 |

OTHER PUBLICATIONS

Chem. Abstract, vol. 88, No. 11 88:7439W, p. 489, (month unavailable) 1978, XP002090974.
Bull. Chem. Soc. of Japan, vol. 46, (month unavailable), 1973, pp. 2215–2218, XP002087557, Isamu Arai, "Reactions of Phenylhydrazinium Thiocyanate With Ketones and Aldehydes".

*Primary Examiner*—Patricia L. Morris
(74) *Attorney, Agent, or Firm*—Joseph C. Gil

(57) ABSTRACT

According to a novel process, it is possible to prepare triazolinethione derivatives of the formula (I)

$$R^1-\underset{\underset{CH_2}{|}}{\overset{\overset{OH}{|}}{C}}-R^2$$

(with triazolinethione ring attached via N)

in which
$R^1$ and $R^2$ are each as defined in the description by
a) reacting hydrazine derivatives of the formula (II)

$$R^1-\underset{\underset{CH_2-NH-NH_2}{|}}{\overset{\overset{OH}{|}}{C}}-R^2$$

or their acid addition salts with an inorganic or organic acid with thiocyanate of the formula $$Y\text{-SCN} \qquad (III)$$

in which
Y represents sodium, potassium or ammonium in the presence of a diluent and, if appropriate, in the presence of a catalyst and
b) reacting the resulting thiosemicarbazide derivatives of the formula (IV)

$$R^1-\underset{\underset{CH_2-N}{|}}{\overset{\overset{OH}{|}}{C}}-R^2 \quad \begin{array}{c} NH_2 \\ / \\ \diagdown \\ C-NH_2 \\ \| \\ S \end{array}$$

with formic acid, if appropriate in the presence of a catalyst and if appropriate in the presence of a diluent. The thiosemicarbazide derivatives of the formula (IV) are novel.

3 Claims, No Drawings

METHOD FOR PRODUCING TRIAZOLINTHION DERIVATIVES

This is a divisional application of Ser. No. 09/509,927, filed Apr. 3, 2000 which is a 371 of PCT/EP 98/06113, filed Sep. 25, 1998.

The present invention relates to a novel process for preparing triazolinethione derivatives which are known as active compounds having microbicidal, in particular fungicidal, properties.

It is already known that triazolinethione derivatives can be prepared by either reacting the corresponding triazole derivatives successively with strong bases and sulphur and then hydrolysing them, or reacting them directly with sulphur at high temperatures, followed by treatment with water (cf. WO-A 96-16 048). However, this process has the disadvantage that the desired products are obtained in only relatively low yields, or that reaction conditions are required which are difficult to maintain on an industrial scale.

Furthermore, it has already been described that certain 1,2,4-triazoline-5-thiones substituted in the 3 position can be prepared by reacting N-chlorolhioformyl-N-(1-chloroalk-1-ene)-amines with carbonylhydrazine derivatives (DE-A 197 01 032, DE-A 196 01 189 and EP-A 0 784 053). However, the synthesis of corresponding substances which do not have a substituent in the 3 position is not mentioned.

Furthermore, Bull. Chem. Soc. Japan 46, 2215 (1973) discloses that triazolinethiones substituted in the 3 position can be synthesized by reacting phenylhydrazine with sodium thiocyanate and ketones or aldehydes in the presence of hydrochloric acid and treating the resulting triazolidenethiones substituted in the 3 position with oxidizing agents. This process has the disadvantages that very long reaction times are required and that no triazolinethiones which are unsubstituted in the 3 position can be obtained in this manner.

Finally, it is also known that 2-(1-chloro-cyclopropyl)-1-(2-chlorophenyl)-3-(1,2,4-triazol-1-yl)-propan-2-ole is obtained when [1-(2-chloro-phenyl)-2-(1-chloro-cyclopropyl)- 2-hydroxy]-propyl-1-hydrazine is reacted with formamidine acetate (cf. DE-A 40 30 039). However, thiono derivatives of triazoles are not obtainable by this method.

It has now been found that triazolinethione derivatives of the formula

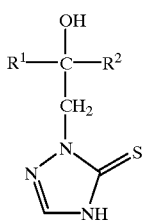

(I)

in which
R¹ and R² are identical or different and each represents optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl,
can be prepared by
a) reacting, in a first step, hydrazine derivatives of the formula

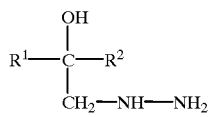

(II)

in which
R¹ and R² are each as defined above,
or their addition salts with an inorganic or organic acid, with thiocyanate of the formula

 Y-SCN (III)

in which
Y represents sodium, potassium or ammonium,
in the presence of a diluent and, if appropriate, in the presence of a catalyst, and
b) reacting the resulting thiosemicarbazide derivatives of the formula

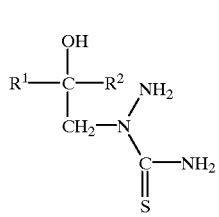

(IV)

in which
R¹ and R² are each as defined above
with formic acid, if appropriate in the presence of a catalyst and if appropriate in the presence of a diluent.

It is extremely surprising that the triazolinethione derivatives of the formula (I) can be prepared by the process according to the invention in substantially higher yields or under considerably more simple conditions than by the prior-art methods. It is likewise unexpected that, in the practice of the first step of the process according to the invention, the attack of the thiocyanate occurs predominantly not at the terminal but at the substituted nitrogen atom of the hydrazine derivative of the formula (11), thus yielding the desired isomer with high selectivity.

The process according to the invention has a number of advantages. Thus, as already mentioned, it is possible to synthesize triazolinethione derivatives of the formula (I) in high yield. It is also favourable that the required starting materials and reaction components can be prepared in a simple manner and are available even in relatively large amounts. A further advantage consists in the fact that the individual steps can be carried out and the reaction products can be isolated without any problems.

Using 2-(1-chloro-cyclopropyl)-3-(2-chloro-phenyl)-2-hydroxy-propyl-1-hydrazonium sulphate as starting material and reacting this in the first step with ammonium thiocyanate and allowing the resulting thiosemicarbazide to react in the second step with fonnic acid, the course of the process according to the invention can be illustrated by the scheme below.

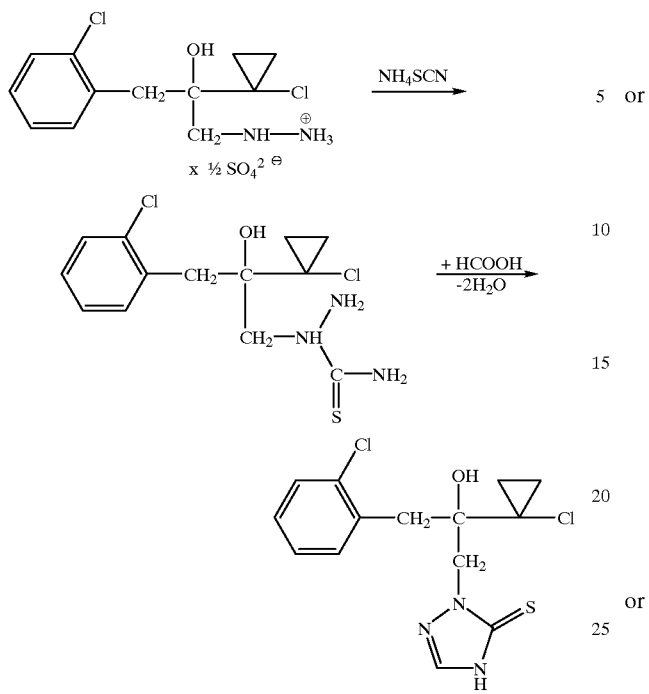

The formula (II) provides a general definition of the hydrazine derivatives required as starting materials for carrying out the process according to the invention. Preference is given to using compounds of the formula (II) in which R¹ represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused 5- or 6-membered heteroaromatic radical having 1 to 3 heteroatoms, such as nitrogen, sulphur and/or oxygen, where each of these radicals may be mono- to trisubstituted by identical or different substituents from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and cyano, and $R^2$ represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the alkyl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused 5- or 6-membered heteroaromatic radical having 1 to 3 heteroatoms, such as nitrogen, sulphur and/or oxygen, where each of these radicals may be mono- to trisubstituted by identical or different substituents from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximino-alkyl having 1 to 4 carbon atoms in the alkoxy moiety and 1 to 3 carbon atoms in the alkyl moiety, nitro and cyano.

Particular preference is given to using hydrazine derivatives of the formula (II) in which $R^1$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-chain or branched alkyl moiety, where the phenyl moiety may he mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluorometlhylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and cyano, formyl, dimethoxyethyl, acetyl and propionyl, and $R^2$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio , methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and cyano, formyl, dimethoxymethyl, acetyl and propionyl.

Very particular preference is given to using hydrazine derivatives of the formula (II) in which $R^1$ represents n-propyl, isopropyl, n-butyl, i-butyl, sec-butyl or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents 1-methyl-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and cyano, formyl, dimethoxymethyl, acetyl and propionyl, and $R^2$ represents n-propyl, isopropyl, n-butyl, i-butyl, sec-butyl or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents 1-methyl-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and cyano, formyl, dimethoxymethyl, acetyl and propionyl.

Preference is also given to using addition salts of the abovementioned preferred or particularly preferred hydrazine derivatives of the formula (II) and an inorganic or organic acid. Preference is given to hydrazonium salts of the formula

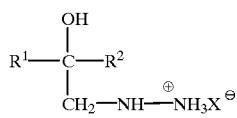

(IIa)

in which

R$^1$ and R$^2$ are each as defined above and

X$^\ominus$ represents chloride or an equivalent of a sulphate anion.

The hydrazine derivatives of the formula (II) are known or can be prepared by processes known in principle (cf. DE-A 40 30 039).

Thus, hydrazine derivatives of the formula (II) are obtained by reacting 1-chloro-2-hydroxy-ethane derivatives of the formula

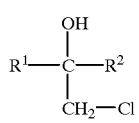

(V)

in which

R$^1$ and R$^2$ are each as defined above with hydrazine hydrate, if appropriate in the presence of a diluent.

The hydrazine derivatives of the formula (II) can be converted into their acid addition salts by reacting them with an inorganic or organic acid in the presence of a diluent.

The 1-chloro-2-hydroxy-ethane derivatives of the formula (V) are known or can be prepared by processes known in principle (cf. DE-A 40 30 039 and EP-A 0 297 345).

Suitable diluents for the above process for preparing hydrazine derivatives of the formula (II) are all customary inert organic solvents. Preference is given to using alcohols, such as methanol, ethanol or n-butanol, furthermore ethers, such as dioxane or methyl tert-butyl ether, and also aromatic hydrocarbons, such as benzene, toluene or xylene. However, it is also possible to carry out the reaction without any additional solvent. In this case, an excess of hydrazine hydrate is employed, so that it acts both as reaction component and as diluent.

When carrying out the preparation of hydrazine derivatives of the formula (II) according to the above process, the reaction temperatures can be varied within a certain range. In general, the process is carried out at temperatures between 60° C. and 120° C., preferably between 70° C. and 110° C.

In the preparation of hydrazine derivatives of the formula (II) according to the above process, in general from 1 to 20 mol, preferably from 5 to 15 mol, of hydrazine hydrate are employed per mole of 1-chloro-2-hydroxy-ethane derivative of the formula (V). Work-up is carried out by customary methods. In general, the reaction mixture is admixed with an organic solvent which is sparingly water-miscible. such as methyl tert-butyl ether or toluene, the aqueous phase is removed and the organic phase is washed and dried.

Suitable diluents for converting the hydrazine derivatives of the formula (II) into their acid addition salts are all organic solvents which are customary for such reactions. Preference is given to using aromatic hydrocarbons, such as benzene, toluene or xylene, or ethers, such as dioxane or methyl tert-butyl ether.

The hydrazine derivatives of the formula (II) are generally converted into salts at room temperature. However, it is also possible to carry out the conversion at a slightly elevated or reduced temperature.

The conversion of hydrazine derivatives of the formula (II) into salts is generally carried out such that a hydrazine derivative of the formula (II) is dissolved in a solvent and mixed with an equivalent amount or an excess of acid. When preparing chlorides, it is possible to use either hydrochloric acid or gaseous hydrogen chloride. The salts can be isolated by customary methods.

The thiocyanates of the formula (III) required as reaction components for carrying out the first step of the process according to the invention are known.

Suitable diluents for carrying out the first step of the process according to the invention are all inert organic solvents which are customary for such reactions. Preference is given to using aromatic hydrocarbons, such as benzene, toluene or xylene, furthermore ethers, such as dioxane or methyl tert-butyl ether, and also esters, such as ethyl acetate.

Suitable catalysts for carrying out the first step of the process according to the invention are all reaction promoters which are customary for such reactions. Preference is given to using water.

When carrying out the first step of the process according to the invention, the reaction temperatures can be varied within a relatively wide range. In general, the reaction is carried out at temperatures between 50° C. and 120° C., preferably between 70° C. and 110° C.

Both the first and the second step of the process according to the invention are generally carried out under atmospheric pressure. However, it is also possible to carry out the process under elevated pressure or, if no gaseous components are involved in the reaction, also under reduced pressure.

When carrying out the first step of the process according to the invention, in general from 1 to 2 mol of thiocyanate of the formula (III) and, if required, a small amount of catalyst are employed per mole of hydrazine derivative of the formula (II). Work-up is carried out by customary methods. In general, the reaction mixture is washed with water, the organic phase is dried and concentrated and the residue that remains is freed from undesirable components by customary methods, for example by chromatography or recrystallization.

The formula (IV) provides a general definition of the thiosemicarbazide derivatives required as starting materials for carrying out the second step of the process according to the invention. In this formula, $R^1$ and $R^2$ each preferably have those meanings which have already been mentioned in connection with the description of the hydrazine derivatives of the formula (II) as being preferred for these radicals.

The thiosemicarbazide derivatives of the formula (IV) have hitherto not been known. They can be prepared by the reaction of the first step of the process according to the invention.

Suitable catalysts for carrying out the second step of the process according to the invention are all reaction promoters which are customary for such reactions. Preference is given to using acids, such as hydrochloric acid or sulphuric acid, and furthermore metal oxides, such as amorphous titanium dioxide.

Suitable diluents for carrying out the second step of the process according to the invention are all weakly polar organic solvents which are customary for such reactions. Preference is given to using esters, such as ethyl acetate or isobutyl formate, and also formic acid.

When carrying out the second step of the process according to the invention, the reaction temperatures can be varied within a certain range. In general, the reaction is carried out at temperatures between 80° C. and 120° C., preferably between 90° C. and 110° C.

When carrying out the second step of the process according to the invention, an excess, in general from 5 to 15 mol, of formic acid and, if required, a small amount of catalyst are employed per mole of thiosemicarbazide derivative of the of the formula (IV). Work-up is carried out by customary methods. In general, the reaction mixture is, if appropriate after prior dilution with an organic solvent that is sparingly water-miscible, extracted with aqueous salt solution, and the organic phase is dried and concentrated. Any impurities which may still be present can then be removed by customary methods, such as recrystallization or chromatography.

In a particular variant, the process according to the invention can be carried out such that 1-chloro-2-hydroxy-ethane derivatives of the formula (V) are reacted with hydrazine hydrate and the resulting hydrazine derivatives of the formula (II) are then reacted further without prior isolation. Accordingly, triazolinethiones of the formula (I) can also be prepared by reacting 1-chloro-2-hydroxy-ethane derivatives of the formula

(V)

in which
$R^1$ and $R^2$ are each as defined above
with hydrazine hydrate, if appropriate in the presence of a diluent, and reacting the resulting hydrazine derivatives of the formula

(II)

in which
$R^1$ and $R^2$ are each as defined above
if appropriate with an inorganic or organic acid in the presence of a diluent,
and reacting the hydrazine derivatives of the formula (II) or their acid addition salts
without prior isolation with thiocyanate of the formula

Y-SCN (III)

in which

Y represents sodium, potassium or ammonium in the presence of a diluent and, if appropriate, in the presence of a catalyst and reacting the resulting thiosemicarbazide derivatives of the formula

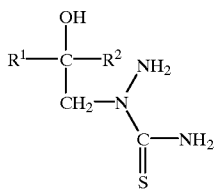

(IV)

in which

R$^1$ and R$^2$ are each as defined above with formic acid, if appropriate in the presence of a catalyst and if appropriate in the presence of a diluent.

When carrying out the individual steps of this process, the procedure which has already been described above is adopted.

The triazolinethione derivatives preparable according to the invention can be present in the "thiono" form of the formula

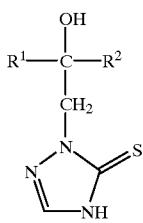

(I)

or in the tautomeric "mercapto" form of the formula

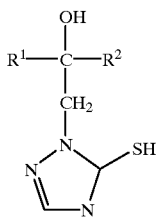

(Ia)

For the sake of simplicity, only the "thiono" form is shown in each case.

The triazolinethione derivatives preparable according to the invention are known as active compounds with microbicidal, in particular fungicidal, properties (cf. WO-A 96-16 048).

The practice of the process according to the invention is illustrated by the examples below.

PREPARATION EXAMPLES

Example 1

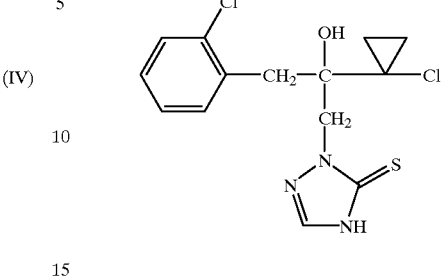

a) Preparation of the compound of the formula

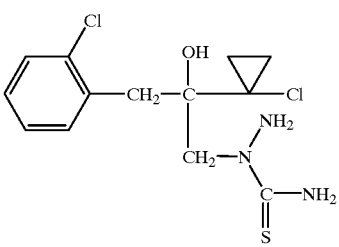

(IV-1)

With stirring, a mixture of 4.86 g (15 mmol) of 2-(1-chloro-cyclopropyl)-3-(2-chloro-phenyl)-2-hydroxy-propyl-1-hydrazonium sulphate, 1.26 g (16.5 mmol) of ammonium thiocyanate and 30 ml of ethyl acetate is heated between 74 and 76° C. for 3 hours. The reaction mixture is then allowed to cool to room temperature and then washed with 20 ml of water. The organic phase is dried over sodium sulphate, filtered and concentrated under reduced pressure. This gives 5.81 g of a product which, according to HPLC analysis, comprises 65.9% of the thiosemicarbazide derivative of the formula (IV-1). Accordingly, the calculated yield is 76.4% of theory. After recrystallization from methanol, the thiosemicarbazide derivative of the formula (IV-1) is obtained in the form of a crystalline solid which melts at from 128 to 129° C.

b) Preparation of the compound of the formula

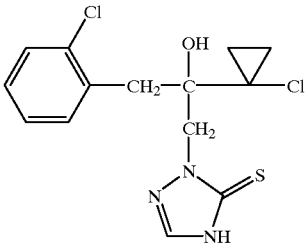

At room temperature, a mixture of 3.35 g (10 mmol) of thiosemicarbazide derivative of the formula (IV-1) in 10 ml of isobutyl formate is admixed with stirring with 5 ml (132 mmol) of formic acid, and the mixture is then heated at 95° C. for 5.5 hours. The reaction mixture is then cooled to room temperature and subsequently diluted with 50 ml of ethyl acetate and washed three times with 10 ml of saturated aqueous to ammonium chloride solution each time. The organic phase is dried over sodium sulphate, filtered and concentrated under reduced pressure. This gives 3.65 g of a product which, according to HPLC analysis, comprises 86.4% of 2-(1-chloro-cyclopropyl)-1-(2-chloro-phenyl)-3-(4,5-dihydro- 1 ,2,4-triazol-5-thiono-1-yl)-propan-2-ole. Accordingly, the calculated yield is 91.6% of theory.

COMPARATIVE EXAMPLES

Example A

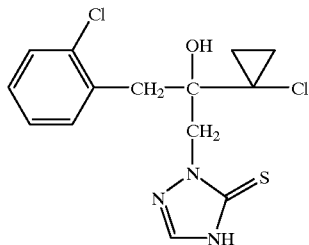

At −20° C., a mixture of 3.12 g (10 mmol) of 2-(1-chloro-cyclopropyl)-1-(2-chlorophenyl)-3-(1,2,4-triazol-1-yl)-propan-2-ole and 45 ml of absolute tetrahydrofuran is admixed with 8.4 ml (21 mmol) of n-butyl-lithium in hexane and stirred at 0° C. for 30 minutes. The reaction mixture is then cooled to −70° C., admixed with 0.32 g (10 mmol) of sulphur powder and stirred at −70° C. for 30 minutes. The mixture is warmed to −10° C., admixed with ice-water and adjusted to pH 5 by addition of dilute sulphuric acid. The mixture is extracted repeatedly with ethyl acetate, and the combined organic phases are dried over sodium sulphate and concentrated under reduced pressure. In this manner, 3.2 g of a product which, according to gas chromatographic analysis, comprises 95% of 2-(1-chloro-cyclopropyl)-1-(2-chloro-phenyl)-3-(4,5-dihydro-1,2,4-triazol-5-thiono-1-yl)-propan-2-ole are obtained. Recrystallization from toluene gives this substance as a solid which melts at from 138 to 139° C.

Example B

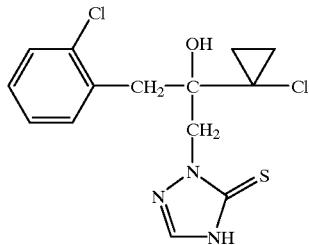

With stirring, a mixture of 3.12 g (10 mmol) of 2-(1-chloro-cyclopropyl)-1-(2-chloro-phenyl)-3-(1,2,4-triazol-1-yl)-propan-2-ole, 0.96 g (30 mmol) of sulphur powder and 20 ml of absolute N-methyl-pyrrolidone is heated at 200° C. for 44 hours. The reaction mixture is then concentrated under reduced pressure (0.2 mbar). The resulting crude product (3.1 g) is recrystallized from toluene. In this manner, 0.7 g (20% of theory) of 2-(1-chloro-cyclopropyl)-1-(2-chloro-phenyl)-3-(4,5-dihydro-1,2,4-triazol-5-thiono-1-yl)-propan-2-ole is obtained in the form of a solid which melts at from 138 to 139° C.

What is claimed is:
1. A thiosemicarbazide derivative of the formula

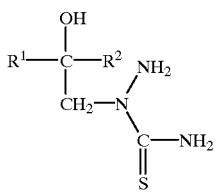

(IV)

wherein
R$^1$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl;
or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl;
or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl;
or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano;
or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano;
or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano;

or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano; and $R^2$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl;

or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl;

or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl;

or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano;

or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano;

or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano;

or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano.

2. A thiosemicarbazide derivative according to claim 1, characterized by the formula

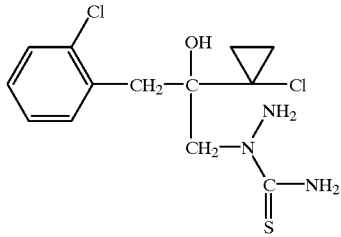

(IV-1)

3. A thiosemicarbazide derivative according to claim 1, wherein $R^1$ represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano; and $R^2$ represents 1-methyl-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl.

* * * * *